United States Patent [19]

Bril et al.

[11] Patent Number: 6,096,517
[45] Date of Patent: Aug. 1, 2000

[54] HUMAN KIDNEY SODIUM BICARBONATE TRANSPORTER (HNBC1A) POLYNUCLEOTIDES

[75] Inventors: Antoine Michel Alain Bril, Saint-Gregoire; Nassirah Khandoudi, Rennes, both of France; Xavier Martin, Pace; Walter F Boron, Orange, both of France

[73] Assignees: SmithKline Beecham Laboratories, New Haven, Conn.; Pharmaceutiques and Yale University School of Medicine, Nanterre Cedex, France

[21] Appl. No.: 09/136,652

[22] Filed: Aug. 19, 1998

[30]     Foreign Application Priority Data

Aug. 19, 1997 [EP]  European Pat. Off. .............. 97401947

[51] Int. Cl.[7] .............................. C12P 21/06; C12N 1/20; C12N 15/00; C07H 21/02
[52] U.S. Cl. .................. 435/69.1; 435/252.3; 435/320.1; 536/23.1
[58] Field of Search .......................... 536/23.1; 435/69.1, 435/252.3, 320.1

[56]              References Cited

PUBLICATIONS

Choi et al. Sodium bicarbonate cotransporter (hhNBC) cloned from human heart cDNA library. Sequence submission: Cellular and molecular Physiology, Yale University, New Haven, CT. Acc. No. AF069510, Jun. 1998.

Burnham et al. "Cloning and Functional Expression of a Human Kidney $Na^+$: $HCO^-_3$ Cotransporter", Journal of Biological Chemistry, vol. 272(31), pp. 19111–19114 (1997).

Romero et al. "Expression cloning and characterization of a renal electrogenic $Na^+/HCO^-_3$ cotransporter", Nature, vol. 387, pp. 409–413 (1997).

GenBank Accession #AF007216.

GenBank Accession #AF001958.

*Primary Examiner*—Karen Cochrane Carlson
*Assistant Examiner*—Holly Schnizer
*Attorney, Agent, or Firm*—William T. Han; Ratner & Prestia; William T. King

[57]                ABSTRACT

HNBC1A polypeptides and polynucleotides and methods for producing such polypeptides by recombinant techniques are disclosed. Also disclosed are methods for utilizing HNBC1A polypeptides and polynucleotides in the design of protocols for the treatment of ischemia heart disease, arrhythmia, congestive heart disease, stroke and renal failure, among others, and diagnostic assays for such conditions.

6 Claims, No Drawings

SEQUENCE LISTING

<160> NUMBER OF SEQ ID NOS: 2

<210> SEQ ID NO 1
<211> LENGTH: 3284
<212> TYPE: DNA
<213> ORGANISM: HOMO SAPIENS

<400> SEQUENCE: 1

```
aggagaagtc tgagcattct ttttttcttt tttattacta taggatggag gatgaagctg        60
tcctggacag agggggcttcc ttcctcaagc atgtgtgtga tgaagaagaa gtagaaggcc       120
accataccat ttacatcgga gtccatgtgc cgaagagtta caggagaagg agacgtcaca       180
agagaaagac agggcacaaa gaaagaaggg aaaaggagag aatctctgag aactactctg       240
acaaatcaga tattgaaaat gctgatgaat ccagcagcag catcctaaaa cctctcatct       300
ctcctgctgc agaacgcatc cgattcatct tgggagagga ggatgacagc ccagctcccc       360
ctcagctctt cacggaactg gatgagctgc tggccgtgga tgggcaggag atggagtgga       420
aggaaacagc caggtggatc aagtttgaag aaaaagtgga acagggtggg gaaagatgga       480
gcaagcccca tgtggccaca ttgtcccttc atagtttatt tgagctgagg acatgtatgg       540
agaaaggatc catcatgctt gatcgggagg cttcttctct cccacagttg gtggagatga       600
ttgttgacca tcagattgag acaggcctat tgaaacctga acttaaggat aaggtgacct       660
atactttgct ccggaagcac cggcatcaaa ccaagaaatc caaccttcgg tccctggctg       720
acattgggaa gacagtctcc agtgcaagta ggatgtttac caaccctgat aatggtagcc       780
cagccatgac ccataggaat ctgacttcct tcagtctgaa tgacatttct gataaaccgg       840
agaaggacca gctgaagaat aagttcatga aaaaattgcc acgtgatgca gaagcttcca       900
acgtgcttgt tggggaggtt gacttttttgg atactccttt cattgccttt gttaggctac       960
agcaggctgt catgctgggt gccctgactg aagttcctgt gccacaaggg ttcttgttca      1020
ttctcttagg tcctaagggg aaagccaagt cctaccacga gattggcaga gccattgcca      1080
ccctgatgtc tgatgaggtg ttccatgaca ttgcttataa agcaaaagac aggcacgacc      1140
```

-continued

```
tgattgctgg tattgatgag ttcctagatg aagtcatcgt ccttccacct ggggaatggg      1200
atccagcaat taggatagag cctcctaaga gtcttccatc ctctgacaaa agaaagaata      1260
tgtactcagg tggagagaat gttcagatga atggggatac gccccatgat ggaggtcacg      1320
gaggaggagg acatggggat tgtgaagaat tgcagcgaac tggacggttc tgtggtggac      1380
taattaaaga cataaagagg aaagcgccat tttttgccag tgattttat gatgctttaa       1440 atattcaagc tctttcggca attctcttca tttatctggc aactgtaact aatgctatca      1500
cttttggagg actgcttggg gatgccactg acaaacatgca gggcgtgttg gagagtttcc    1560
tgggcactgc tgtctctgga gccatctttt gcctttttgc tggtcaacca ctcactattc      1620
tgagcagcac cggacctgtc ctagttttg agaggcttct atttaatttc agcaaggaca      1680
ataattttga ctatttggaa tttcgccttt ggattggcct gtggtccgcc ttcctatgtc      1740
tcattttggt agccactgat gccagcttct tggttcaata cttcacacgt ttcacggagg      1800
agggcttttc ctctctgatt agcttcatct ttatctatga tgctttcaag aagatgatca     1860
agcttgcaga ttactacccc atcaactcca acttcaaagt gggctacaac actctctttt      1920
cctgtacctg tgtgccacct gacccagcta atatctcaat atctaatgac accacactgg     1980
ccccagagta tttgccaact atgtcttcta ctgacatgta ccataatact acctttgact     2040 gggcatttt gtcgaagaag gagtgttcaa aatacggagg aaacctcgtc gggaacaact     2100
gtaattttgt tcctgatatc acactcatgt cttttatcct cttcttggga acctacacct     2160
cttccatggc tctgaaaaaa ttcaaaacta gtccttattt tccaaccaca gcaagaaaac     2220
tgatcagtga ttttgccatt atcttgtcca ttctcatctt ttgtgtaata gatgccctag     2280
taggcgtgga cacccccaaaa ctaattgtgc caagtgagtt caagccaaca agtccaaacc    2340
gaggttggtt cgttccaccg tttggagaaa acccctggtg ggtgtgcctt gctgctgcta     2400
tcccggcttt gttggtcact atactgattt tcatggacca acaaattaca gctgtgattg     2460
taaacaggaa agaacataaa ctcaagaaag gagcagggta tcacttggat ctcttttggg     2520
tggccatcct catggttata tgctccctca tggctcttcc gtggtatgta gctgctacgg     2580
tcatctccat tgctcacatc gacagtttga agatggagac agagacttct gcacctggag     2640
aacaaccaaa gtttctagga gtgagggaac aaagagtcac tggaaccctt gtgtttattc     2700
tgactggtct gtcagtcttt atggctccca tcttgaagtt tatacccatg cctgtactct     2760
atggtgtgtt cctgtatatg ggagtagcat cccttaatgg tgtgcagttc atggatcgtc    2820
tgaagctgct tctgatgcct ctgaagcatc agcctgactt catctacctg cgtcatgttc     2880
ctctgcgcag agtccacctg ttcacttttcc tgcaggtgtt gtgtctggcc ctgctttga     2940 tcctcaagtc aacggtggct gctatcattt ttccagtaat gatcttggca cttgtagctg     3000
tcagaaaagg catggactac ctcttctccc agcatgacct cagcttcctg gatgatgtca     3060
ttccagaaaa ggacaagaaa aagaaggagg atgagaagaa aagaaaaag aagaagggaa     3120 gtctggacag tgacaatgat gattctgact gcccatactc agaaaaagtt ccaagtatta     3180
aaattccaat ggacatcatg gaacagcaac cttttcctaag cgatagcaaa ccttctgaca    3240
gagaaagatc accaacattc cttgaacgcc acacatcatg ctga                      3284
```

<210> SEQ ID NO 2
<211> LENGTH: 1079
<212> TYPE: PRT
<213> ORGANISM: HOMO SAPIENS

-continued

<400> SEQUENCE: 2

```
Met Glu Asp Glu Ala Val Leu Asp Arg Gly Ala Ser Phe Leu Lys His
  1               5                  10                  15
Val Cys Asp Glu Glu Val Gly His His Thr Ile Tyr Ile Gly
             20                  25                  30
Val His Val Pro Lys Ser Tyr Arg Arg Arg Arg His Lys Arg Lys
             35                  40                  45
Thr Gly His Lys Glu Lys Lys Glu Lys Glu Arg Ile Ser Glu Asn Tyr
         50                  55                  60
Ser Asp Lys Ser Asp Ile Glu Asn Ala Asp Glu Ser Ser Ser Ser Ile
 65                  70                  75                  80
Leu Lys Pro Leu Ile Ser Pro Ala Ala Glu Arg Ile Arg Phe Ile Leu
                     85                  90                  95
Gly Glu Glu Asp Asp Ser Pro Ala Pro Pro Gln Leu Phe Thr Glu Leu
                100                 105                 110
Asp Glu Leu Leu Ala Val Asp Gly Gln Glu Met Glu Trp Lys Glu Thr
            115                 120                 125
Ala Arg Trp Ile Lys Phe Glu Glu Lys Val Glu Gln Gly Gly Glu Arg
        130                 135                 140
Trp Ser Lys Pro His Val Ala Thr Leu Ser Leu His Ser Leu Phe Glu
145                 150                 155                 160
Leu Arg Thr Cys Met Glu Lys Gly Ser Ile Met Leu Asp Arg Glu Ala
                    165                 170                 175
Ser Ser Leu Pro Gln Leu Val Glu Met Ile Val Asp His Gln Ile Glu
                180                 185                 190
Thr Gly Leu Leu Lys Pro Glu Leu Lys Asp Lys Val Thr Tyr Thr Leu
            195                 200                 205
Leu Arg Lys His Arg His Gln Thr Lys Lys Ser Asn Leu Arg Ser Leu
        210                 215                 220
Ala Asp Ile Gly Lys Thr Val Ser Ser Ala Ser Arg Met Phe Thr Asn
225                 230                 235                 240
Pro Asp Asn Gly Ser Pro Ala Met Thr His Arg Asn Leu Thr Ser Phe
                    245                 250                 255
Ser Leu Asn Asp Ile Ser Asp Lys Pro Glu Lys Asp Gln Leu Lys Asn
                260                 265                 270
Lys Phe Met Lys Lys Leu Pro Arg Asp Ala Glu Ala Ser Asn Val Leu
            275                 280                 285
Val Gly Glu Val Asp Phe Leu Asp Thr Pro Phe Ile Ala Phe Val Arg
        290                 295                 300
Leu Gln Gln Ala Val Met Leu Gly Ala Leu Thr Glu Val Pro Val Pro
305                 310                 315                 320
Thr Arg Phe Leu Phe Ile Leu Leu Gly Pro Lys Gly Lys Ala Lys Ser
                    325                 330                 335
Tyr His Glu Ile Gly Arg Ala Ile Ala Thr Leu Met Ser Asp Glu Val
                340                 345                 350
Phe His Asp Ile Ala Tyr Lys Ala Lys Asp Arg His Asp Leu Ile Ala
            355                 360                 365
Gly Ile Asp Glu Phe Leu Asp Glu Val Ile Val Leu Pro Pro Gly Glu
        370                 375                 380
Trp Asp Pro Ala Ile Arg Ile Glu Pro Lys Ser Leu Pro Ser Ser
385                 390                 395                 400
Asp Lys Arg Lys Asn Met Tyr Ser Gly Gly Glu Asn Val Gln Met Asn
                    405                 410                 415
```

-continued

```
Gly Asp Thr Pro His Asp Gly His Gly Gly Gly His Gly Asp
            420                 425                 430
Cys Glu Glu Leu Gln Arg Thr Gly Arg Phe Cys Gly Gly Leu Ile Lys
            435                 440                 445
Asp Ile Lys Arg Lys Ala Pro Phe Phe Ala Ser Asp Phe Tyr Asp Ala
450                 455                 460
Leu Asn Ile Gln Ala Leu Ser Ala Ile Leu Phe Ile Tyr Leu Ala Thr
465                 470                 475                 480
Val Thr Asn Ala Ile Thr Phe Gly Gly Leu Leu Gly Asp Ala Thr Asp
                485                 490                 495
Asn Met Gln Gly Val Leu Glu Ser Phe Leu Gly Thr Ala Val Ser Gly
            500                 505                 510
Ala Ile Phe Cys Leu Phe Ala Gly Gln Pro Leu Thr Ile Leu Ser Ser
            515                 520                 525
Thr Gly Pro Val Leu Val Phe Glu Arg Leu Leu Phe Asn Phe Ser Lys
            530                 535                 540
Asp Asn Asn Phe Asp Tyr Leu Glu Phe Arg Leu Trp Ile Gly Leu Trp
545                 550                 555                 560
Ser Ala Phe Leu Cys Leu Ile Leu Val Ala Thr Asp Ala Ser Phe Leu
                565                 570                 575
Val Gln Tyr Phe Thr Arg Phe Thr Glu Gly Phe Ser Ser Leu Ile
            580                 585                 590
Ser Phe Ile Phe Ile Tyr Asp Ala Phe Lys Lys Met Ile Lys Leu Ala
            595                 600                 605
Asp Tyr Tyr Pro Ile Asn Ser Asn Phe Lys Val Gly Tyr Asn Thr Leu
            610                 615                 620
Phe Ser Cys Thr Cys Val Pro Pro Asp Pro Ala Asn Ile Ser Ile Ser
625                 630                 635                 640
Asn Asp Thr Thr Leu Ala Pro Glu Tyr Leu Pro Thr Met Ser Ser Thr
                645                 650                 655
Asp Met Tyr His Asn Thr Thr Phe Asp Trp Ala Phe Leu Ser Lys Lys
            660                 665                 670
Glu Cys Ser Lys Tyr Gly Gly Asn Leu Val Gly Asn Asn Cys Asn Phe
            675                 680                 685
Val Pro Asp Ile Thr Leu Met Ser Phe Ile Leu Phe Leu Gly Thr Tyr
            690                 695                 700
Thr Ser Ser Met Ala Leu Lys Lys Phe Lys Thr Ser Pro Tyr Phe Pro
705                 710                 715                 720
Thr Thr Ala Arg Lys Leu Ile Ser Asp Phe Ala Ile Ile Leu Ser Ile
                725                 730                 735
Leu Ile Phe Cys Val Ile Asp Ala Leu Val Gly Val Asp Thr Pro Lys
            740                 745                 750
Leu Ile Val Pro Ser Glu Phe Lys Pro Thr Ser Pro Asn Arg Gly Trp
            755                 760                 765
Phe Val Pro Pro Phe Gly Glu Asn Pro Trp Trp Val Cys Leu Ala Ala
            770                 775                 780
Ala Ile Pro Ala Leu Leu Val Thr Ile Leu Ile Phe Met Asp Gln Gln
785                 790                 795                 800
Ile Thr Ala Val Ile Val Asn Arg Lys Glu His Lys Leu Lys Lys Gly
                805                 810                 815
Ala Gly Tyr His Leu Asp Leu Phe Trp Val Ala Ile Leu Met Val Ile
            820                 825                 830
```

-continued

```
Cys Ser Leu Met Ala Leu Pro Trp Tyr Val Ala Ala Thr Val Ile Ser
        835             840             845

Ile Ala His Ile Asp Ser Leu Lys Met Glu Thr Glu Thr Ser Ala Pro
    850             855             860

Gly Glu Gln Pro Lys Phe Leu Gly Val Arg Glu Gln Arg Val Thr Gly
865             870             875             880

Thr Leu Val Phe Ile Leu Thr Gly Leu Ser Val Phe Met Ala Pro Ile
                885             890             895

Leu Lys Phe Ile Pro Met Pro Val Leu Tyr Gly Val Phe Leu Tyr Met
            900             905             910

Gly Val Ala Ser Leu Asn Gly Val Gln Phe Met Asp Arg Leu Lys Leu
        915             920             925

Leu Leu Met Pro Leu Lys His Gln Pro Asp Phe Ile Tyr Leu Arg His
    930             935             940

Val Pro Leu Arg Arg Val His Leu Phe Thr Phe Leu Gln Val Leu Cys
945             950             955             960

Leu Ala Leu Leu Trp Ile Leu Lys Ser Thr Val Ala Ala Ile Ile Phe
            965             970             975

Pro Val Met Ile Leu Ala Leu Val Ala Val Arg Lys Gly Met Asp Tyr
            980             985             990

Leu Phe Ser Gln His Asp Leu Ser Phe Leu Asp Asp Val Ile Pro Glu
        995             1000            1005

Lys Asp Lys Lys Lys Glu Asp Glu Lys Lys Lys Lys Lys Lys
        1010            1015            1020

Gly Ser Leu Asp Ser Asp Asn Asp Asp Ser Asp Cys Pro Tyr Ser Glu
1025            1030            1035            104

Lys Val Pro Ser Ile Lys Ile Pro Met Asp Ile Met Glu Gln Gln Pro
                1045            1050            1055

Phe Leu Ser Asp Ser Lys Pro Ser Asp Arg Glu Arg Ser Pro Thr Phe
            1060            1065            1070

Leu Glu Arg His Thr Ser Cys
            1075
```

HUMAN KIDNEY SODIUM BICARBONATE TRANSPORTER (HNBC1A) POLYNUCLEOTIDES

FIELD OF INVENTION

This invention relates to newly identified splice-variant polynucleotides, polypeptides encoded by them and to the use of such polynucleotides and polypeptides, and to their production. More particularly, the polynucleotides and polypeptides of the present invention relate to the sodium bicarbonate co-transporter family, hereinafter referred to as NBC1A. The invention also relates to inhibiting or activating the action of such polynucleotides and polypeptides.

BACKGROUND OF THE INVENTION

The sodium bicarbonate co-transporter, hereinafter called "Na+/HCO3— co-transporter", is one of the mechanisms involved in the regulation of intracellular pH. Acidosis established during myocardial ischemia stimulates this system. Extrusion of protons through Na+/HCO3—co-transporter is accompanied by cellular uptake of Na+ leading to more dangerous Ca2+ overload due to the functioning of Na+/Ca2+ exchanger in reverse-mode. This implies that specific inhibition of Na+/HCO3—co-transporter will be of benefit in reduction of cellular injury during ischemia.

A human kidney sodium bicarbonate transporter (NBC) has recently been described (Burnham et al., J Biol Chem, 272; 19111–19114, 1997). In addition, an electrogenic Na+ bicarbonate cotransporter of *Ambystoma tigrinum* has also been recently described (Romero et al., Nature, 387; 409–413, 1997).

This suggests that members of the sodium bicarbonate co-transporter family may have potential use as therapeutic targets. Consequently there is a need for identification and characterization of further members of the sodium bicarbonate co-transporter family which may play a role in preventing, ameliorating or correcting dysfunctions or diseases, including, but not limited to, ischaemia heart disease, arrhythmias, congestive heart disease, stroke and renal failure,

SUMMARY OF THE INVENTION

The HNBC1A polynucleotides of the invention are splice variants of the human NBC gene; the polypeptide sequence of SEQ ID NO:2 is identical to the published NBC polypeptide sequence (Burnham et al., J Biol Chem, 272; 19111–19114, 1997) in the C-terminal 994 amino acid residues, with the exception of the phenylalanine at position 256 in SEQ ID NO:2, which is a serine at the corresponding position in the published sequence. The N-terminal 85 amino acid residues of SEQ ID NO:2 differ from the N-terminal 41 amino acid residues of the published NBC polypeptide sequence.

In one aspect, the invention relates to HNBC1A polypeptides and recombinant materials and methods for their production. Another aspect of the invention relates to methods for using such HNBC1A polypeptides and polynucleotides. Such uses include the treatment of ischemia heart disease, arrhythmias, congestive heart disease, stroke and renal failure, among others. In still another aspect, the invention relates to methods to identify agonists and antagonists using the materials provided by the invention, and treating conditions associated with HNBC1A imbalance with the identified compounds. Yet another aspect of the invention relates to diagnostic assays for detecting diseases associated with inappropriate HNBC1A activity or levels.

DESCRIPTION OF THE INVENTION

Definitions

The following definitions are provided to facilitate understanding of certain terms used frequently herein.

"HNBC1A" refers, among others, generally to a polypeptide having the amino acid sequence set forth in SEQ ID NO:2 or an allelic variant thereof.

"HNBC1A activity or HNBC1A polypeptide activity" or "biological activity of the HNBC1A or HNBC1A polypeptide" refers to the metabolic or physiological function of said HNBC1A including similar activities or improved activities or these activities with decreased undesirable side-effects. Also included are antigenic and immunogenic activities of said HNBC1A.

"HNBC1A gene" refers to a polynucleotide having the nucleotide sequence set forth in SEQ ID NO:1 or allelic variants thereof and/or their complements.

"Antibodies" as used herein includes polyclonal and monoclonal antibodies, chimeric, single chain, and humanized antibodies, as well as Fab fragments, including the products of an Fab or other immunoglobulin expression library.

"Isolated" means altered "by the hand of man" from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide separated from the coexisting materials of its natural state is "isolated", as the term is employed herein.

"Polynucleotide" generally refers to any polyribonucleotide or polydeoxribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosinie. A variety of modifications has been made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short polynucleotides, often referred to as oligonucleotides.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from posttranslation natural processes or may be made by synthetic methods. Modifications include acetylation, acylation, ADP-ribosylation, amidation, biotinylation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. See, for instance, PROTEINS—STRUCTURE AND MOLECULAR PROPERTIES, 2nd Ed., T. E. Creighton, W. H. Freeman and Company, New York, 1993 and Wold, F., Posttranslational Protein Modifications: Perspectives and Prospects, pgs. 1–12 in POST-TRANSLATIONAL COVALENT MODIFICATION OF PROTEINS, B. C. Johnson, Ed., Academic Press, New York, 1983; Seifter et al., "Analysis for protein modifications and nonprotein cofactors", *Meth Enzyntol* (1990) 182:626–646 and Rattan et al., "Protein Synthesis: Posttranslational Modifications and Aging", *Ann NY Acad Sci* (1992) 663:48–62.

"Variant" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusions and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques or by direct synthesis.

"Identity" is a measure of the identity of nucleotide sequences or amino acid sequences. In general, the sequences are aligned so that the highest order match is obtained. "Identity" per se has an art-recognized meaning and can be calculated using published techniques. See, e.g.: (COMPUTATIONAL MOLECULAR BIOLOGY, Lesk, A. M., ed., Oxford University Press, New York, 1988; BIO-COMPUTING: INFORMATICS AND GENOME PROJECTS, Smith, D. W., ed., Academic Press, New York, 1993; COMPUTER ANALYSIS OF SEQUENCE DATA, PART I, Griffin, A. M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity between two polynucleotide or polypeptide sequences, the term "identity" is well known to skilled artisans (Carillo, H., and Lipton, D., *SIAM J Applied Math* (1988)48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., *SIAM J Applied Math* (1988) 48:1073. Methods to determine identity and similarity are codified in computer programs. Preferred computer program methods to determine identity and similarity between two sequences include, but are not limited to those in the GCG or Lasergene software packages.

Polypeptides of the Invention

In one aspect, the present invention relates to HNBC1A polypeptides (or HNBC1A proteins). The HNBC1A polypeptides include the polypeptide of SEQ ID NO:2; as well as polypeptides comprising the amino acid sequence of SEQ ID NO:2. Preferably HNBC1A polypeptide exhibit at least one biological activity of HNBC1A.

The HNBC1A polypeptides may be in the form of the "mature" protein or may be a part of a larger protein such as a precursor or fusion protein. It is often advantageous to include an additional amino acid sequence which contains secretory or leader sequences, pro-sequences, sequences which aid in purification such as multiple histidine residues, or an additional sequence for stability during recombinant production.

Fragments of the HNBC1A polypeptides are also included in the invention. A fragment is a polypeptide having an amino acid sequence that entirely is the same as part, but not all, of the amino acid sequence of the aforementioned HNBC1A polypeptides. As with HNBC1A polypeptides, fragments may be "free-standing," or comprised within a larger polypeptide of which they form a part or region, most preferably as a single continuous region. Representative examples of polypeptide fragments of the invention, include, for example, fragments from about amino acid number 1–20, 21–40, 41–60, 61–80, 81–100, and 101 to the end of HNBC1A polypeptide. In this context "about" includes the particularly recited ranges larger or smaller by several, 5, 4, 3, 2 or 1 amino acid at either extreme or at both extremes.

Preferred fragments include, for example, truncation polypeptides having the amino acid sequence of HNBC1A polypeptides, except for deletion of a continuous series of residues that includes the amino terminus, or a continuous series of residues that includes the carboxyl terminus or deletion of two continuous series of residues, one including the amino terminus and one including the carboxyl terminus. Also preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Other preferred fragments are biologically active fragments. Biologically active fragments are those that mediate HNBC1A activity, including those with a similar activity or an improved activity, or with a decreased undesirable activity. Also included are those that are antigenic or immunogenic in an animal, especially in a human.

Preferably, all of these polypeptide fragments retain the biological activity of the HNBC1A, including antigenic activity. Variants of the defined sequence and fragments also form part of the present invention. Preferred variants are those that vary from the referents by conservative amino acid substitutions—i.e., those that substitute a residue with another of like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, or 1–2 amino acids are substituted, deleted, or added in any combination.

The HNBC1A polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

Polynucleotides of the Invention

Another aspect of the invention relates to HNBC1A polynucleotides. HNBC1A polynucleotides include isolated polynucleotides which encode the HNBC1A polypeptides and fragments, and polynucleotides closely related thereto. More specifically, HNBC1A polynucleotide of the invention include a polynucleotide comprising the nucleotide sequence contained in SEQ ID NO:1 encoding a HNBC1A polypeptide of SEQ ID NO:2, and polynucleotides having the particular sequence of SEQ ID NO:1. The invention also provides polynucleotides which are complementary to such HNBC1A polynucleotides.

HNBC1A of the invention is structurally related to other proteins of thesodium bicarbonate co-transporter family, as shown by the results of sequencing the cDNA encoding human HNBC1A. HNBC1A is a splice variant of the human kidney NBC (Burnham et al., J Biol Chem, 272; 19111–19114, 1997). Furthermore amino acid sequence of SEQ ID NO:2 is 87.3% identical to electrogenic Na+ bicarbonate cotransporter of Ambystoma tigrinum over 1014 amino acid residues (Romero et al., Nature, 387; 409–413, 1997). Thus HNBC1A polypeptides and polynucleotides of the present invention are expected to have, inter alia, similar biological functions/properties to their homologous polypeptides and polynucleotides, and their utility is obvious to anyone skilled in the art.

One polynucleotide of the present invention encoding HNBC1A may be obtained using standard cloning and screening, from a cDNA library derived from mRNA in cells of human cardiac tissue using the expressed sequence tag (EST) analysis (Adams, M. D., et al. Science (1991) 252:1651–1656; Adams, M. D. et al, *Nature*, (1992) 355:632–634; Adams, M. D., et al., *Nature* (1995) 377 Supp:3–174). Polynucleotides of the invention can also be obtained from natural sources such as genomic DNA libraries or can be synthesized using well known and commercially available techniques.

The nucleotide sequence encoding HNBC1A polypeptide of SEQ ID NO:2 may be identical to the polypeptide encoding sequence contained in SEQ ID NO:1 (nucleotide number 45 to 3284 of SEQ ID NO:1), or it may be a sequence, which as a result of the redundancy (degeneracy) of the genetic code, also encodes the polypeptide of SEQ ID NO:2.

When the polynucleotides of the invention are used for the recombinant production of HNBC1A polypeptide, the polynucleotide may include the coding sequence for the mature polypeptide or a fragment thereof, by itself; the coding sequence for the mature polypeptide or fragment in reading frame with other coding sequences, such as those encoding a leader or secretory sequence, a pre-, or pro- or prepro-protein sequence, or other fusion peptide portions. For example, a marker sequence which facilitates purification of the fused polypeptide can be encoded. In certain preferred embodiments of this aspect of the invention, the marker sequence is a hexa-histidine peptide, as provided in the pQE vector (Qiagen, Inc.) and described in Gentz et al, *Proc Natl Acad Sci USA* (1989) 86:821–824, or is an HA tag. The polynucleotide may also contain non-coding 5' and 3' sequences, such as transcribed, non-translated sequences, splicing and polyadenylation signals, ribosome binding sites and sequences that stabilize mRNA.

Further preferred embodiments are polynucleotides encoding HNBC1A variants comprising the amino acid sequence of HNBC1A polypeptide of SEQ ID NO:2 in which several, 5–10, 1–5, 1–3, 1–2 or 1 amino acid residues are substituted, deleted or added, in any combination.

The present invention further relates to polynucleotides that hybridize to the herein above-described sequences. In this regard, the present invention especially relates topolynucleotides which hybridize under stringent conditions to the herein above-described polynucleotides. As herein used, the term "stringent conditions" means hybridization will occur only if there is at least 80%, and preferably at least 90%, and more preferably at least 95%, yet even more preferably 97–99% identity between the sequences.

Polynucleotides of the invention, which are identical or sufficiently identical to a nucleotide sequence contained in SEQ ID NO:1 or a fragment, may be used as hybridization probes for cDNA and genomic DNA, to isolate full-length cDNAs and genomic clones encoding HNBC1A polypeptide and to isolate cDNA and genomic clones of other genes (including genes encoding homologs and orthologs from species other than human) that have a high sequence similarity to the HNBC1A gene. Such hybridization techniques are known to those of skill in the art. Typically these nucleotide sequences are 80% identical, preferably 90% identical, more preferably 95% identical to that of the referent. The probes generally will comprise at least 15 nucleotides. Preferably, such probes will have at least 30 nucleotides and may have at least 50 nucleotides. Particularly preferred probes will range between 30 and 50 nucleotides.

In one embodiment, to obtain a polynucleotide encoding HNBC1A polypeptide, including homologs and orthologs from species other than human, comprises the steps of screening an appropriate library under stingent hybridization conditions with a labeled probe having the SEQ ID NO:1 or a fragment thereof, and isolating full-length cDNA and genomic clones containing said polynucleotide sequence. Such hybridization techniques are well known to those of skill in the art. Thus in another aspect, HNBC1A polynucleotides of the present invention further include a nucleotide sequence comprising a nucleotide sequence that hybridize under stringent condition to a nucleotide sequence having SEQ ID NO:1 or a fragment thereof. Also included with HNBC1A polypeptides are polypeptide comprising amino acid sequence encoded by nucleotide sequence obtained by the above hybridization condition. Stringent hybridization conditions are as defined above or, alternatively, conditions under overnight incubation at 42° C. in a solution comprising: 50% formamide, 5×SSC (150 mM NaCl, 15 mM trisodium citrate), 50 mM sodium phosphate (pH 7.6), 5× Denhardt's solution, 10% dextran sulfate, and 20 microgram/ml denatured, sheared salmon sperm DNA, followed by washing the filters in 0.1×SSC at about 65° C.

The polynucleotides and polypeptides of the present invention may be employed as research reagents and materials for discovery of treatments and diagnostics to animal and human disease.

Vectors, Host Cells, Expression

The present invention also relates to vectors which comprise a polynucleotide or polynucleotides of the present invention, and host cells which are genetically engineered with vectors of the invention and to the production of polypeptides of the invention by recombinant techniques. Cell-free translation systems can also be employed to produce such proteins using RNAs derived from the DNA constructs of the present invention.

For recombinant production, host cells can be genetically engineered to incorporate expression systems or portions thereof for polynucleotides of the present invention. Introduction of polynucleotides into host cells can be effected by methods described in many standard laboratory manuals, such as Davis et al., *BASIC METHODS IN MOLECULAR BIOLOGY* (1986) and Sambrook et al., *MOLECULAR CLONING: A LABORATORY MANUAL*, 2nd Ed., Cold Spring Harbor Laboratory Press, Cold Spring Harbor, N.Y. (1989) such as calcium phosphate transfection, DEAE-dextran mediated transfection, transvection, microinjection, cationic lipid-mediated transfection, electroporation, transduction, scrape loading, ballistic introduction or infection.

Representative examples of appropriate hosts include bacterial cells, such as streptococci, staphylococci, *E. coli*, Streptomyces and *Bacillus subtilis* cells; fungal cells, such as yeast cells and Aspergillus cells; insect cells such as Drosophila S2 and Spodoptera Sf9 cells; animal cells such as CHO, COS, HeLa, C127, 3T3, BHK, HEK 293 and Bowes melanoma cells; and plant cells.

A great variety of expression systems can be used. Such systems include, among others, chromosomal, episomal and virus-derived systems, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retrovirtises, and vectors derived from combinations thereof, such as those derived from plasmid and bacteriophage genetic elements, such as cosmids and phagemids. The expression systems may contain control regions that regulate as well as engender expression. Generally, any system or vector suitable to maintain, propagate or express polynucleotides to produce a polypeptide in a host may be used. The appropriate nucleotide sequence may be inserted into an expression system by any of a variety of well-known and routine techniques, such as, for example, those set forth in Sambrook et al., *MOLECULAR CLONING, A LABORATORY MANUAL* (supra).

For secretion of the translated protein into the lumen of the endoplasmic reticulum, into the periplasmic space or into the extracellular environment, appropriate secretion signals may be incorporated into the desired polypeptide. These signals may be endogenous to the polypeptide or they may be heterologous signals.

If the HNBC1A polypeptide is to be expressed for use in screening assays, generally, it is preferred that the polypeptide be produced at the surface of the cell. In this event, the cells may be harvested prior to use in the screening assay. If HNBC1A polypeptide is secreted into the medium, the medium can be recovered in order to recover and purify the polypeptide; if produced intracellularly, the cells must first be lysed before the polypeptide is recovered. HNBC1A polypeptides can be recovered and purified from recombinant cell cultures by well known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography is employed for purification. Well known techniques for refolding proteins may be employed to regenerate active conformation when the polypeptide is denatured during isolation and or purification.

Diagnostic Assays

This invention also relates to the use of HNBC1A polynucleotides for use as diagnostic reagents. Detection of a mutated form of HNBC1A gene associated with a dysfunction will provide a diagnostic tool that can add to or define a diagnosis of a disease or susceptibility to a disease which results from under-expression, over-expression or altered expression of HNBC1A. Individuals carrying mutations in the HNBC1A gene may be detected at the DNA level by a variety of techniques.

Nucleic acids for diagnosis may be obtained from a subject's cells, such as from blood, urine, saliva, tissue biopsy or autopsy material. The genomic DNA may be used directly for detection or may be amplified enzymatically by using PCR or other amplification techniques prior to analysis. RNA or cDNA may also be used in similar fashion. Deletions and insertions can be detected by a change in size of the amplified product in comparison to the normal genotype. Point mutations can be identified by hybridizing amplified DNA to labeled HNBC1A nucleotide sequences. Perfectly matched sequences can be distinguished from mismatched duplexes by RNase digestion or by differences in melting temperatures. DNA sequence differences may also be detected by alterations in electrophoretic mobility of DNA fragments in gels, with or without denaturing agents, or by direct DNA sequencing. See, e.g., Myers et al., *Science* (1985) 230:1242. Sequence changes at specific locations may also be revealed by nuclease protection assays, such as RNase and S1 protection or the chemical cleavage method. See Cotton et al., *Proc Natl Acad Sci USA* (1985) 85:4397–4401. In another embodiment, an array of oligonucleotides probes comprising HNBC1A nucleotide sequence or fragments thereof can be constructed to conduct efficient screening of e.g., genetic mutations. Array technology methods are well known and have general applicability and can be used to address a variety of questions in molecular genetics including gene expression, genetic linkage, and genetic variability. (See for example: M. Chee et al., *Science*, Vol 274, pp 610–613 (1996)).

The diagnostic assays offer a process for diagnosing or determining a susceptibility to ischaemia heart disease, arrhythmias, congestive heart disease, stroke and renal failure through detection of mutation in the HNBC1A gene by the methods described.

In addition, ischaemia heart disease, arrhythmias, congestive heart disease, stroke and renal failure, can be diagnosed by methods comprising determining from a sample derived from a subject an abnormally decreased or increased level of HNBC1A polypeptide or HNBC1A mRNA. Decreased or increased expression can be measured at the RNA level using any of the methods well known in the art for the quantitation of polynucleotides, such as, for example, PCR, RT-PCR, RNase protection, Northern blotting and other hybridization methods. Assay techniques that can be used to determine levels of a protein, such as an HNBC1A polypeptide, in a sample derived from a host are well-known to those of skill in the art. Such assay methods include radioimmunoassays, competitive-binding assays, Western Blot analysis and ELISA assays.

Thus in another aspect, the present invention relates to a diagnostic kit for a disease or suspectability to a disease, particularly ischaemia heart disease, arrhythmias, congestive heart disease, stroke and renal failure, which comprises:

(a) a HNBC1A polynucleotide, preferably the nucleotide sequence of SEQ ID NO:1, or a fragment thereof;

(b) a nucleotide sequence complementary to that of (a);

(c) a HNBC1A polypeptide, preferably the polypeptide of SEQ ID NO:2, or a fragment thereof; or (d) an antibody to a HNBC1A polypeptide, preferably to the polypeptide of SEQ ID NO:2. It will be appreciated that in any such kit, (a), (b), (c) or (d) may comprise a substantial component.

Chromosome Assays

The nucleotide sequences of the present invention are also valuable for chromosome identification. The sequence is specifically targeted to and can hybridize with a particular location on an individual human chromosome. The mapping of relevant sequences to chromosomes according to the present invention is an important first step in correlating those sequences with gene associated disease. Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes). The differences in the cDNA or genomic sequence between affected and unaffected individuals can also be determined. If a mutation is observed in some or all of the affected individuals but not in any normal individuals, then the mutation is likely to be the causative agent of the disease.

Antibodies

The polypeptides of the invention or their fragments or analogs thereof, or cells expressing them can also be used as immunogens to produce antibodies immunospecific for the HNBC1A polypeptides. The term "immunospecific" means that the antibodies have substantiall greater affinity for the polypeptides of the invention than their affinity for other related polypeptides in the prior art.

Antibodies generated against the HNBC1A polypeptides can be obtained by administering the polypeptides or epitope-bearing fragments, analogs or cells to an animal, preferably a nonhuman, using routine protocols. For preparation of monoclonal antibodies, any technique which provides antibodies produced by continuous cell line cultures can be used. Examples include the hybridoma technique (Kohler, G. and Milstein, C., Nature (1975) 256:495–497), the trioma technique, the human B-cell hybridoma technique (Kozbor et al., Immunology Today (1983)4:72) and the EBV-hybridoma technique (Cole el al., MONOCLONAL ANTIBODIES AND CANCER THERAPY, pp. 77–96, Alan R. Liss, Inc., 1985).

Techniques for the production of single chain antibodies (U.S. Pat. No. 4,946,778) can also be adapted to produce single chain antibodies to polypeptides of this invention. Also, transgenic mice, or other organisms including other mammals, may be used to express humanized antibodies.

The above-described antibodies may be employed to isolate or to identify clones expressing the polypeptide or to purify the polypeptides by affinity chromatography.

Antibodies against HNBC1A polypeptides may also be employed to treat ischaemia heart disease, arrhythmias, congestive heart disease, stroke and renal failure, among others.

Vaccines

Another aspect of the invention relates to a method for inducing an immunological response in a mammal which comprises inoculating the mammal with HNBC1A polypeptide, or a fragment thereof, adequate to produce antibody and/or T cell immune response to protect said animal from ischaemia heart disease, arrhythmias, congestive heart disease, stroke and renal failure, among others. Yet another aspect of the invention relates to a method of inducing immunological response in a mammal which comprises, delivering HNBC1A polypeptide via a vector directing expression of HNBC1A polynucleotide in vivo in order to induce such an immunological response to produce antibody to protect said animal from diseases.

Further aspect of the invention relates to an immunological/vaccine formulation (composition) which, when introduced into a mammalian host, induces an immunological response in that mammal to a HNBC1A polypeptide wherein the composition comprises a HNBC1A polypeptide or HNBC1A gene. The vaccine formulation may further comprise a suitable carrier. Since HNBC1A polypeptide may be broken down in the stomach, it is preferably administered parenterally (including subcutaneous, intramuscular, intravenous, intradermal etc. injection). Formulations suitable for parenteral administration include aqueous and non-aqueous sterile injection solutions which may contain anti-oxidants, buffers, bacteriostats and solutes which render the formulation instonic with the blood of the recipient; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

Screening Assays

The HNBC1A polypeptide of the present invention may be employed in a screening process for compounds which activate (agonists) or inhibit activation of (antagonists, or otherwise called inhibitors) the HNBC1A polypeptide of the present invention. Thus, polypeptides of the invention may also be used to assess identify agonist or antagonists from, for example, cells, cell-free preparations, chemical libraries, and natural product mixtures. These agonists or antagonists may be natural or modified substrates, ligands, enzymes, receptors, etc., as the case may be, of the polypeptide of the present invention; or may be structural or functional mimetics of the polypeptide of the present invention. See Coligan el al., *Current Protocols in Immunology* 1(2):Chapter 5 (1991).

HNBC1A polypeptides are responsible for many biological functions, including many pathologies. Accordingly, it is desirous to find compounds and drugs which stimulate HNBC1A polypeptide on the one hand and which can inhibit the function of HNBC1A polypeptide on the other hand. In general, agonists are employed for therapeutic and prophylactic purposes for such conditions as ischaemia heart disease, arrhythmias, congestive heart disease, stroke and renal failure Antagonists may be employed for a variety of therapeutic and prophylactic purposes for such conditions as ischaemia heart disease, arrhythmias, congestive heart disease, stroke and renal failure.

In general, such screening procedures may involve using appropriate cells which express the HNBC1A polypeptide or respond to HNBC1A polypeptide of the present invention. Such cells include cells from mammals, yeast, Drosophila or *E. coli*. Cells which express the HNBC1A polypeptide (or cell membrane containing the expressed polypeptide) or respond to HNBC1A polypeptide are then contacted with a test compound to observe binding, or stimulation or inhibition of a functional response. The ability of the cells which were contacted with the candidate compounds is compared with the same cells which were not contacted for HNBC1A activity.

The assays may simply test binding of a candidate compound wherein adherence to the cells bearing the HNBC1A polypeptide is detected by means of a label directly or indirectly associated with the candidate compound or in an assay involving competition with a labeled competitor. Further, these assays may test whether the candidate compound results in a signal generated by activation of the HNBC1A polypeptide, using detection systems appropriate to the cells bearing the HNBC1A polypeptide. Inhibitors of activation are generally assayed in the presence of a known agonist and the effect on activation by the agonist by the presence of the candidate compound is observed.

Further, the assays may simply comprise the steps of mixing a candidate compound with a solution containing a HNBC1A polypeptide to form a mixture, measuring HNBC1A activity in the mixture, and comparing the HNBC1A activity of the mixture to a standard.

The HNBC1A cDNA, protein and antibodies to the protein may also be used to configure assays for detecting the effect of added compounds on the production of HNBC1A mRNA and protein in cells. For example, an ELISA may be constructed for measuring secreted or cell associated levels of HNBC1A protein using monoclonal and polyclonal antibodies by standard methods known in the art, and this can be used to discover agents which may inhibit or enhance the production of HNBC1A (also called antagonist or agonist, respectively) from suitably manipulated cells or tissues.

The HNBC1A protein may be used to identify membrane bound or soluble receptors, if any, through standard receptor binding techniques known in the art. These include, but are not limited to, ligand binding and crosslinking assays in which the HNBC1A is labeled with a radioactive isotope (eg 125I), chemically modified (eg biotinylated), or fused to a peptide sequence suitable for detection or purification, and incubated with a source of the putative receptor (cells, cell membranes, cell supernatants, tissue extracts, bodily fluids). Other methods include biophysical techniques such as surface plasmon resonance and spectroscopy. In addition to being used for purification and cloning of the receptor, these binding assays can be used to identify agonists and antagonists of HNBC1A which compete with the binding of HNBC1A to its receptors, if any. Standard methods for conducting screening assays are well understood in the art.

Examples of potential HNBC1A polypeptide antagonists include antibodies or, in some cases, oligonucleotides or proteins which are closely related to the ligands, substrates, enzymes, receptors, etc., as the case may be, of the HNBC1A polypeptide, e.g., a fragment of the ligands, substrates, enzymes, receptors, etc.; or small molecules which bind to the polypeptide of the present invention but do not elicit a response, so that the activity of the polypeptide is prevented.

Thus in another aspect, the present invention relates to a screening kit for identifying agonists, antagonists, ligands, receptors, substrates, enzymes, etc. for HNBC1A polypeptides; or compounds which decrease or enhance the production of HNBC1A polypeptides, which comprises:

(a) a HNBC1A polypeptide, preferably that of SEQ ID NO:2;

(b) a recombinant cell expressing a HNBC1A polypeptide, preferably that of SEQ ID NO:2;

(c) a cell membrane expressing a HNBC1 A polypeptide; preferably that of SEQ ID NO: 2; or (d) antibody to a HNBC1A polypeptide, preferably that of SEQ ID NO:2. It will be appreciated that in any such kit, (a), (b), (c) or (d) may comprise a substantial component.

Prophylactic and Therapeutic Methods

This invention provides methods of treating abnormal conditions such as, ischaemia heart disease, arrhythmias, congestive heart disease, stroke and renal failure, related to both an excess of and insufficient amounts of HNBC1A polypeptide activity.

If the activity of HNBC1A polypeptide is in excess, several approaches are available. One approach comprises administering to a subject an inhibitor compound (antagonist) as hereinabove described along with a pharmaceutically acceptable carrier in an amount effective to inhibit the function of the HNBC1A polypeptide, such as, for example, by blocking the binding of ligands, substrates, enzymes, receptors, etc., or by inhibiting a second signal, and thereby alleviating the abnormal condition. In another approach, soluble forms of HNBC1A polypeptides still capable of binding the ligand, substrate, enzymes, receptors, etc. in competition with endogenous HNBC1A polypeptide may be administered. Typical embodiments of such competitors comprise fragments of the HNBC1A polypeptide.

In another approach, soluble forms of HNBC1A polypeptides still capable of binding the ligand in competition with endogenous HNBC1A polypeptide may be administered. Typical embodiments of such competitors comprise fragments of the HNBC1A polypeptide.

In still another approach, expression of the gene encoding endogenous HNBC1A polypeptide can be inhibited using expression blocking techniques. Known such techniques involve the use of antisense sequences, either internally generated or externally administered. See, for example, O'Connor, *J Neurochem* (1991) 56:560 in *Oligodeoxynucleotides as Antisense Inhibitors of Gene Expression*, CRC Press, Boca Raton, Fla. (1988). Alternatively, oligonucleotides which form triple helices with the gene can be supplied. See, for example, Lee et al., *Nucleic Acids Res* (1979) 6:3073; Cooney et al., *Science* (1988) 241:456; Dervan et al., *Science* (1991) 251:1360. These oligomers can be administered per se or the relevant oligomers can be expressed in vivo.

For treating abnormal conditions related to an under-expression of HNBC1A and its activity, several approaches are also available. One approach comprises administering to a subject a therapeutically effective amount of a compound which activates HNBC1A polypeptide, i.e., an agonist as described above, in combination with a pharmaceutically acceptable carrier, to thereby alleviate the abnormal condition. Alternatively, gene therapy may be employed to effect the endogenous production of HNBC1A by the relevant cells in the subject. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a subject for engineering cells in vivo and expression of the polypeptide in vivo. For overview of gene therapy, see Chapter 20, *Gene Therapy and other Molecular Genetic-based Therapeutic Approaches*, (and references cited therein) in Human Molecular Genetics, T Strachan and A P Read, BIOS Scientific Publishers Ltd (1996). Another approach is to administer therapeutic amount of HNBC1A polypeptides in combination with a suitable pharmaceutical carrier.

Formulation and Administration

Peptides, such as the soluble form of HNBC1A polypeptides, and agonists and antagonist peptides or small molecules, may be formulated in combination with a suitable pharmaceutical carrier. Such formulations comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. Formulation should suit the mode of administration, and is well within the skill of the art. The invention further relates to pharmaceutical packs and kits comprising one or more containers filled with one or more of the ingredients of the aforementioned compositions of the invention.

Polypeptides and other compounds of the present invention may be employed alone or in conjunction with other compounds, such as therapeutic compounds.

Preferred forms of systemic administration of the pharmaceutical compositions include injection, typically by intravenous injection. Other injection routes, such as subcutaneous, intramuscular, or intraperitoneal, can be used. Alternative means for systemic administration include trans-mucosal and transdermal administration using penetrants such as bile salts or fusidic acids or other detergents. In addition, if properly formulated in enteric or encapsulated formulations, oral administration may also be possible. Administration of these compounds may also be topical and/or localized, in the form of salves, pastes, gels and the like.

The dosage range required depends on the choice of peptide, the route of administration, the nature of the formulation, the nature of the subject's condition, and the judgment of the attending practitioner. Suitable dosages, however, are in the range of 0.1–100 µg/kg of subject. Wide variations in the needed dosage, however, are to be expected in view of the variety of compounds available and the differing efficiencies of various routes of administration. For example, oral administration would be expected to require higher dosages than administration by intravenous injection. Variations in these dosage levels can be adjusted using standard empirical routines for optimization, as is well understood in the art.

Polypeptides used in treatment can also be generated endogenously in the subject, in treatment modalities often referred to as "gene therapy" as described above. Thus, for example, cells from a subject may be engineered with a polynucleotide, such as a DNA or RNA, to encode a polypeptide ex vivo, and for example, by the use of a retroviral plasmid vector. The cells are then introduced into the subject.

All publications, including but not limited to patents and patent applications, cited in this specification are herein incorporated by reference as if each individual publication were specifically and individually indicated to be incorporated by reference herein as though fully set forth.

Sequence information

```
SEQ ID NO:1
AGGAGAAGTCTGAGCATTCTTTTTTTCTTTTTTATTACTATAGGATGGAGGATGAAGCTGTCCTGGACAGAG

GGGCTTCCTTCCTCAAGCATGTGTGTGATGAAGAAGAAGTAGAAGGCCACCATACCATTTACATCGGAGTCC

ATGTGCCGAAGAGTTACAGGAGAAGGAGACGTCACAAGAGAAAGACAGGGCACAAAGAAAAGAAGGAAAAGG

AGAGAATCTCTGAGAACTACTCTGACAAATCAGATATTGAAAATGCTGATGAATCCAGCAGCAGCATCCTAA

AACCTCTCATCTCTCCTGCTGCAGAACGCATCCGATTCATCTTGGGAGAGGAGGATGACAGCCCAGCTCCCC

CTCAGCTCTTCACGGAACTGGATGAGCTGCTGGCCGTGGATGGGCAGGAGATGGAGTGGAAGGAAACAGCCA

GGTGGATCAAGTTTGAAGAAAAAGTGGAACAGGGTGGGGAAAGATGGAGCAAGCCCCATGTGGCCACATTGT

CCCTTCATAGTTTATTTGAGCTGAGGACATGTATGGAGAAAGGATCCATCATGCTTGATCGGGAGGCTTCTT
```

```
CTCTCCCACAGTTGGTGGAGATGATTGTTGACCATCAGATTGAGACAGGCCTATTGAAACCTGAACTTAAGG
ATAAGGTGACCTATACTTTGCTCCGGAAGCACCGGCATCAAACCAAGAAATCCAACCTTCGGTCCCTGGCTG
ACATTGGGAAGACAGTCTCCAGTGCAAGTAGGATGTTTACCAACCCTGATAATGGTAGCCCAGCCATGACCC
ATAGGAATCTGACTTCCTTCAGTCTGAATGACATTTCTGATAAACCGGAGAAGGACCAGCTGAAGAATAAGT
TCATGAAAAAATTGCCACGTGATGCAGAAGCTTCCAACGTGCTTGTTGGGGAGGTTGACTTTTTGGATACTC
CTTTCATTGCCTTTGTTAGGCTACAGCAGGCTGTCATGCTGGGTGCCCTGACTGAAGTTCCTGTGCCCACAA
GGTTCTTGTTCATTCTCTTAGGTCCTAAGGGGAAAGCCAAGTCCTACCACGAGATTGGCAGAGCCATTGCCA
CCCTGATGTCTGATGAGGTGTTCCATGACATTGCTTATAAAGCAAAAGACAGGCACGACCTGATTGCTGGTA
TTGATGAGTTCCTAGATGAAGTCATCGTCCTTCCACCTGGGGAATGGGATCCAGCAATTAGGATAGAGCCTC
CTAAGAGTCTTCCATCCTCTGACAAAAGAAAGAATATGTACTCAGGTGGAGAGAATGTTCAGATGAATGGGG
ATACGCCCCATGATGGAGGTCACGGAGGAGGAGGACATGGGATTGTGAAGAATTGCAGCGAACTGGACGGT
TCTGTGGTGGACTAATTAAAGACATAAAGAGGAAAGCGCCATTTTTTGCCAGTGATTTTTATGATGCTTTAA
ATATTCAAGCTCTTTCGGCAATTCTCTTCATTTATCTGGCAACTGTAACTAATGCTATCACTTTTGGAGGAC
TGCTTGGGGATGCCACTGACAACATGCAGGGCGTGTTGGAGAGTTTCCTGGGCACTGCTGTCTCTGGAGCCA
TCTTTTGCCTTTTTGCTGGTCAACCACTCACTATTCTGAGCAGCACCGGACCTGTCCTAGTTTTTGAGAGGC
TTCTATTTAATTTCAGCAAGGACAATAATTTTGACTATTTGGAATTTCGCCTTTGGATTGGCCTGTGGTCCG
CCTTCCTATGTCTCATTTTGGTAGCCACTGATGCCAGCTTCTTGGTTCAATACTTCACACGTTTCACGGAGG
AGGGCTTTTCCTCTCTGATTAGCTTCATCTTTATCTATGATGCTTTCAAGAAGATGATCAAGCTTGCAGATT
ACTACCCCATCAACTCCAACTTCAAAGTGGGCTACAACACTCTCTTTTCCTGTACCTGTGTGCCACCTGACC
CAGCTAATATCTCAATATCTAATGACACCACACTGGCCCCAGAGTATTTGCCAACTATGTCTTCTACTGACA
TGTACCATAATACTACCTTTGACTGGGCATTTTTGTCGAAGAAGGAGTGTTCAAAATACGGAGGAAACCTCG
TCGGGAACAACTGTAATTTTGTTCCTGATATCACACTCATGTCTTTTATCCTCTTCTTGGGAACCTACACCT
CTTCCATGGCTCTGAAAAAATTCAAAACTAGTCCTTATTTTCCAACCACAGCAAGAAAACTGATCAGTGATT
TTGCCATTATCTTGTCCATTCTCATCTTTTGTGTAATAGATGCCCTAGTAGGCGTGGACACCCCAAAACTAA
TTGTGCCAAGTGAGTTCAAGCCAACAAGTCCAAACCGAGGTTGGTTCGTTCCACCGTTTGGAGAAAACCCCT
GGTGGGTGTGCCTTGCTGCTGCTATCCCGGCTTTGTTGGTCACTATACTGATTTTCATGGACCAACAAATTA
CAGCTGTGATTGTAAACAGGAAAGAACATAAACTCAAGAAAGGAGCAGGGTATCACTTGGATCTCTTTTGGG
TGGCCATCCTCATGGTTATATGCTCCCTCATGGCTCTTCCGTGGTATGTAGCTGCTACGGTCATCTCCATTG
CTCACATCGACAGTTTGAAGATGGAGACAGAGACTTCTGCACCTGGAGAACAACCAAAGTTTCTAGGAGTGA
GGGAACAAAGAGTCACTGGAACCCTTGTGTTTATTCTGACTGGTCTGTCAGTCTTTATGGCTCCCATCTTGA
AGTTTATACCCATGCCTGTACTCTATGGTGTGTTCCTGTATATGGGAGTAGCATCCCTTAATGGTGTGCAGT
TCATGGATCGTCTGAAGCTGCTTCTGATGCCTCTGAAGCATCAGCCTGACTTCATCTACCTGCGTCATGTTC
CTCTGCGCAGAGTCCACCTGTTCACTTTCCTGCAGGTGTTGTGTCTGGCCCTGCTTTGGATCCTCAAGTCAA
CGGTGGCTGCTATCATTTTTCCAGTAATGATCTTGGCACTTGTAGCTGTCAGAAAAGGCATGGACTACCTCT
TCTCCCAGCATGACCTCAGCTTCCTGGATGATGTCATTCCAGAAAAGGACAAGAAAAAGAAGGAGGATGAGA
AGAAAAAGAAAAAGAAGAAGGGAAGTCTGGACAGTGACAATGATGATTCTGACTGCCCATACTCAGAAAAAG
TTCCAAGTATTAAAATTCCAATGGACATCATGGAACAGCAACCTTTCCTAAGCGATAGCAAACCTTCTGACA
GAGAAAGATCACCAACATTCCTTGAACGCCACACATCATGCTGA
```

SEQ ID NO:2
MEDEAVLDRGASFLKHVCDEEEVEGHHTIYIGVHVPKSYRRRRRHKRKTGHKEKKEKERISENYSDKSDIEN
ADESSSSILKPLISPAAERIRFILGEEDDSPAPPQLFTELDELLAVDGQEMEWKETARWIKFEEKVEQGGER

-continued

WSKPHVATLSLHSLFELRTCMEKGSIMLDREASSLPQLVEMIVDHQIETGLLKPELKDKVTYTLLRKHRHQT
KKSNLRSLADIGKTVSSASRMFTNPDNGSPAMTHRNLTSFSLNDISDKPEKDQLKNKFMKKLPRDAEASNVL
VGEVDFLDTPFIAFVRLQQAVMLGALTEVPVPTRFLFILLGPKGKAKSYHEIGRAIATLMSDEVFHDIAYKA
KDRHDLIAGIDEFLDEVIVLPPGEWDPAIRIEPPKSLPSSDKRKNMYSGGENVQMNGDTPHDGGHGGGHGD
CEELQRTGRFCGGLIKDIKRKAPFFASDFYDALNIQALSAILFIYLATVTNAITFGGLLGDATDNMQGVLES
FLGTAVSGAIFCLFAGQPLTILSSTGPVLVFERLLFNFSKDNNFDYLEFRLWIGLWSAFLCLILVATDASFL
VQYFTRFTEEGFSSLISFIFIYDAFKKMIKLADYYPINSNFKVGYNTLFSCTCVPPDPANISISNDTTLAPE
YLPTMSSTDMYHNTTFDWAFLSKKECSKYGGNLVGNNCNFVPDITLMSFILFLGTYTSSMALKKFKTSPYFP
TTARKLISDFAIILSILIFCVIDALVGVDTPKLIVPSEFKPTSPNRGWFVPPFGENPWWVCLAAAIPALLVT
ILIFMDQQITAVIVNRKEHKLKKGAGYHLDLFWVAILMVICSLMALPWYVAATVISIAHIDSLKMETETSAP
GEQPKFLGVREQRVTGTLVFILTGLSVFMAPILKFIPMPVLYGVFLYMGVASLNGVQFMDRLKLLLMPLKHQ
PDFIYLRHVPLRRVHLFTFLQVLCLALLWILKSTVAAIIFPVMILALVAVRKGMDYLFSQHDLSFLDDVIPE
KDKKKKEDEKKKKKKKGSLDSDNDDSDCPYSEKVPSIKIPMDIMEQQPFLSDSKPSDRERSPTFLERHTSC

What is claimed is:

1. An isolated polynucleotide selected from the group consisting of:
   (i) an isolated polynucleotide comprising a nucleotide sequence encoding the polypeptide of SEQ ID NO:2; or
   (ii) an isolated polynucleotide which is the polynucleotide of SEQ ID NO: 1; or a nucleotide sequence complementary to said isolated polynucleotide.

2. An expression system comprising a polynucleotide capable of producing a polypeptide selected from the group consisting of:
   (i) a polypeptide comprising the amino acid sequence of SEQ ID NO: 2 or
   (ii) a polypeptide which is the amino acid sequence of SEQ ID NO: 2 wherein said expression system is present in a compatible host cell.

3. A process for producing a recombinant host cell comprising transforming or transfecting a cell with the expression system of claim 2 such that the host cell, under appropriate culture conditions, produces a polypeptide comprising the amino acid sequence of SEQ ID NO:2.

4. A recombinant host cell produced by the process of claim 3.

5. A membrane of a recombinant host cell of claim 4 expressing a polypeptide comprising the amino acid sequence of SEQ ID NO:2.

6. A process for producing a polypeptide comprising culturing a host cell of claim 4 under conditions sufficient for the production of said polypeptide and recovering the polypeptide from the culture.

* * * * *